US010728995B2

(12) United States Patent
Kim

(10) Patent No.: US 10,728,995 B2
(45) Date of Patent: *Jul. 28, 2020

(54) MOBILE X-RAY APPARATUS

(71) Applicant: SAMSUNG ELECTRONICS CO., LTD., Suwon-si (KR)

(72) Inventor: Myeong-je Kim, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/356,668

(22) Filed: Mar. 18, 2019

(65) Prior Publication Data
US 2019/0215939 A1 Jul. 11, 2019

Related U.S. Application Data

(63) Continuation of application No. 15/961,502, filed on Apr. 24, 2018, now Pat. No. 10,251,252, which is a
(Continued)

(30) Foreign Application Priority Data

Aug. 3, 2016 (KR) .................. 10-2016-0099133

(51) Int. Cl.
H05G 1/54 (2006.01)
H01M 10/42 (2006.01)
(Continued)

(52) U.S. Cl.
CPC ............ *H05G 1/54* (2013.01); *H01M 10/425* (2013.01); *H01M 10/48* (2013.01); *H02J 7/008* (2013.01);
(Continued)

(58) Field of Classification Search
CPC . H05G 1/54; H05G 1/46; H02J 7/0029; H02J 7/008; H02J 7/025; H02J 2007/0039; H02J 2007/004
See application file for complete search history.

(56) References Cited

U.S. PATENT DOCUMENTS 4,200,912 A 4/1980 Harrington et al.
5,808,376 A 9/1998 Gordon et al.
(Continued)

FOREIGN PATENT DOCUMENTS

EP 2865333 A1 4/2015
JP 200264947 A 2/2002
(Continued)

OTHER PUBLICATIONS

Communication dated Aug. 17, 2017, issued by the Korean Intellectual Property Office in counterpart Korean Application No. 10-2016-0099133.
(Continued)

Primary Examiner — Chih-Cheng Kao
(74) Attorney, Agent, or Firm — Sughrue Mion, PLLC

(57) ABSTRACT

A mobile X-ray apparatus includes: an X-ray radiation device configured to emit X-rays; a controller configured to control the X-ray radiation device; a power supply configured to supply operating power to the X-ray radiation device and the controller; and a charger configured to charge the power supply. The power supply includes a lithium ion battery including a plurality of battery cells, at least one current sensor configured to detect current of the lithium ion battery, and a battery management system (BMS) configured to detect an occurrence of an overcurrent in the lithium ion battery via the at least one current sensor in response to receiving an X-ray emission preparation signal, and to control an on-state or an off-state of a discharge current path
(Continued)

in which a discharge current flows from the lithium ion battery to the controller and the X-ray radiation device.

17 Claims, 11 Drawing Sheets

Related U.S. Application Data continuation of application No. 15/370,679, filed on Dec. 6, 2016, now Pat. No. 9,980,358.

(51) Int. Cl.
| | |
|---|---|
| *H01M 10/48* | (2006.01) |
| *H02J 7/00* | (2006.01) |
| *H02J 7/02* | (2016.01) |
| *H05G 1/46* | (2006.01) |
| *H01M 10/44* | (2006.01) |
| *H01M 10/0525* | (2010.01) |
| *A61B 6/00* | (2006.01) |

(52) U.S. Cl.
CPC ............ *H02J 7/0029* (2013.01); *H02J 7/025* (2013.01); *H05G 1/46* (2013.01); *A61B 6/4405* (2013.01); *A61B 6/56* (2013.01); *H01M 10/0525* (2013.01); *H01M 10/4257* (2013.01); *H01M 10/44* (2013.01); *H01M 2010/4271* (2013.01); *H02J 7/0031* (2013.01); *H02J 7/00304* (2020.01); *H02J 7/00306* (2020.01)

(56) References Cited

U.S. PATENT DOCUMENTS

| | | | |
|---|---|---|---|
| 5,955,869 A | 9/1999 | Rathmann | |
| 7,022,290 B2 | 4/2006 | Gural et al. | |
| 8,030,898 B2 | 10/2011 | Okuto | |
| 8,218,726 B2 | 7/2012 | Bressel | |
| 8,690,425 B2 | 4/2014 | Kopcienski et al. | |
| 8,798,235 B2 | 8/2014 | Ohta et al. | |
| 8,798,236 B2 | 8/2014 | Ohta et al. | |
| 8,929,510 B2 | 1/2015 | Nishino et al. | |
| 8,963,499 B2 | 2/2015 | Choi | |
| 9,044,191 B2 | 6/2015 | Nishino et al. | |
| 9,168,016 B2 | 10/2015 | Ohta et al. | |
| 9,186,117 B2 | 11/2015 | Ogura et al. | |
| 9,655,582 B2 | 5/2017 | Shirota et al. | |
| 9,980,358 B2 * | 5/2018 | Kim | H01M 10/425 |
| 10,251,252 B2 * | 4/2019 | Kim | H02J 7/008 |

| | | |
|---|---|---|
| 2002/0195996 A1 | 12/2002 | Nakatsuji |
| 2008/0278116 A1 | 11/2008 | Matsunaga |
| 2009/0190718 A1 | 7/2009 | Fan |
| 2011/0006731 A1 | 1/2011 | Wang et al. |
| 2011/0110498 A1 | 5/2011 | Takae et al. |
| 2011/0117396 A1 | 5/2011 | Yang et al. |
| 2011/0193525 A1 | 8/2011 | Ro |
| 2012/0027177 A1 | 2/2012 | Ogata et al. |
| 2012/0256099 A1 | 10/2012 | Gregerson et al. |
| 2012/0268066 A1 | 10/2012 | Endo et al. |
| 2013/0127418 A1 | 5/2013 | Oh et al. |
| 2013/0230142 A1 | 9/2013 | Murata et al. |
| 2014/0017546 A1 | 1/2014 | Yanagi |
| 2014/0167704 A1 | 6/2014 | Lafontaine et al. |
| 2015/0245456 A1 | 8/2015 | Nishino et al. |
| 2015/0318720 A1 | 11/2015 | Aradachi et al. |
| 2016/0007432 A1 | 1/2016 | Ohta et al. |
| 2016/0089985 A1 | 3/2016 | Murayama et al. |
| 2016/0315487 A1 | 10/2016 | Shim |
| 2017/0086776 A1 | 3/2017 | Kim |
| 2017/0374728 A1 | 12/2017 | Kuranisi |
| 2018/0000443 A1 | 1/2018 | Matsuura et al. |
| 2018/0014396 A1 | 1/2018 | Imamura |
| 2018/0035524 A1 | 2/2018 | Matsuura |

FOREIGN PATENT DOCUMENTS

| | | |
|---|---|---|
| JP | 2005-147822 A | 6/2005 |
| JP | 2007267559 A | 10/2007 |
| JP | 2010273827 A | 12/2010 |
| JP | 201342643 A | 2/2013 |
| JP | 20143846 A | 1/2014 |
| JP | 2015-118773 A | 6/2015 |
| KR | 10-2001-0008484 A | 2/2001 |
| KR | 101075037 B1 | 10/2011 |
| KR | 101097272 B1 | 12/2011 |
| KR | 20120037682 A | 4/2012 |
| KR | 10-2014-0060801 A | 5/2014 |
| KR | 20150047749 A | 5/2015 |
| KR | 10-2016-0125852 A | 11/2016 |

OTHER PUBLICATIONS

Communication dated Aug. 4, 2017, issued by the European Patent Office in counterpart European Application No. 16207528.7.
Communication dated Feb. 5, 2018, issued by the Korean Intellectual Property Office in corresponding Korean Application No. 10-2016-0099133.
Communication dated Jan. 8, 2020, issued by the European Patent Office in counterpart European Application No. 19171986.3.

\* cited by examiner

MOBILE X-RAY APPARATUS

CROSS-REFERENCE TO RELATED APPLICATIONS

This application is a continuation of U.S. application Ser. No. 15/961,502 filed Apr. 24, 2018, which is a continuation of U.S. patent application Ser. No. 15/370,679 filed Dec. 6, 2016, which claims priority from Korean Patent Application No. 10-2016-0099133, filed Aug. 3, 2016, in the Korean Intellectual Property Office. The disclosures of above-named applications are incorporated herein in their entireties by reference.

BACKGROUND

1. Field

Apparatuses and methods consistent with exemplary embodiments relate to X-ray apparatuses using a lithium ion battery.

2. Description of the Related Art

X-rays are electromagnetic waves having wavelengths of 0.01 to 100 angstroms (Å), and are widely used, due to their ability to penetrate objects, in medical apparatuses for imaging the inside of a living body or in non-destructive testing equipment for industrial use.

An X-ray apparatus using X-rays may obtain X-ray images of an object by transmitting X-rays emitted from an X-ray source through an object and detecting a difference in intensities of the transmitted X-rays via an X-ray detector. The X-ray images may be used to examine an internal structure of an object and diagnose a disease of the object. The X-ray apparatus facilitates observation of an internal structure of an object by using a principle in which penetrating power of an X-ray varies depending on the density of the object and atomic numbers of atoms constituting the object. As a wavelength of an X-ray decreases, penetrating power of the X-ray increases and an image on a screen becomes brighter.

SUMMARY

One or more exemplary embodiments may provide a mobile X-ray apparatus including lithium ion batteries.

According to an aspect of an exemplary embodiment, a mobile X-ray apparatus includes: an X-ray radiation device; a controller configured to control the X-ray radiation device; a power supply configured to supply operating power to the X-ray radiation device and the controller via a lithium ion battery and control overcurrent that occurs during X-ray emission by the X-ray radiation device; and a charger configured to charge the power supply.

The power supply may include: a battery management system (BMS) configured to detect a state of the power supply and control an operation of the power supply; a discharge field effect transistor (FET) configured to control the overcurrent and including a plurality of FETs connected in parallel; and a charge FET.

The discharge FET and the charge FET may be further configured to control a path of a discharge current or a charge current when the lithium ion battery is discharged or charged.

The BMS may be further configured to detect the state of the power supply and control a charge path and a discharge path by turning on/off the discharge FET and the charge FET.

The BMS may be further configured to control an operation of a protection circuit for protection against at least one of over-discharge, overcurrent, overheating, and unbalancing between cells in the lithium ion battery.

The power supply may further include a large-capacity current sensor and a small-capacity current sensor, and the BMS may be further configured to detect, during the X-ray emission by the X-ray radiation device, the overcurrent by activating the large-capacity current sensor.

The mobile X-ray apparatus may further include a current sensor located at an output terminal of the charger in order to detect a charge current.

The controller, the power supply, and the charger may each be embodied in a different module.

The power supply may include a temperature sensor configured to detect a temperature within the power supply, and the controller may be further configured to directly monitor information about a temperature detected by the temperature sensor.

The power supply and the charger may respectively include interrupt pins that can be directly controlled by the controller, and the controller may be further configured to respectively turn off the power supply and the charger via the interrupt pins.

The charger may be a wireless charging system composed of a transmitting module and a receiving module.

The charger may be further configured to receive power wirelessly from the outside and charge the power supply based on the received power.

The charger may be further configured to stop charging of the power supply when a low current state, where a charge current is less than a specific reference value, remains for a specific amount of time.

The charger may be further configured to restart the charging of the power supply when a voltage of the lithium ion battery is lower than a specific reference value.

BRIEF DESCRIPTION OF THE DRAWINGS

The above and/or other aspects will become more apparent by describing certain exemplary embodiments, with reference to the accompanying drawings, in which.

DETAILED DESCRIPTION

Figure 1:
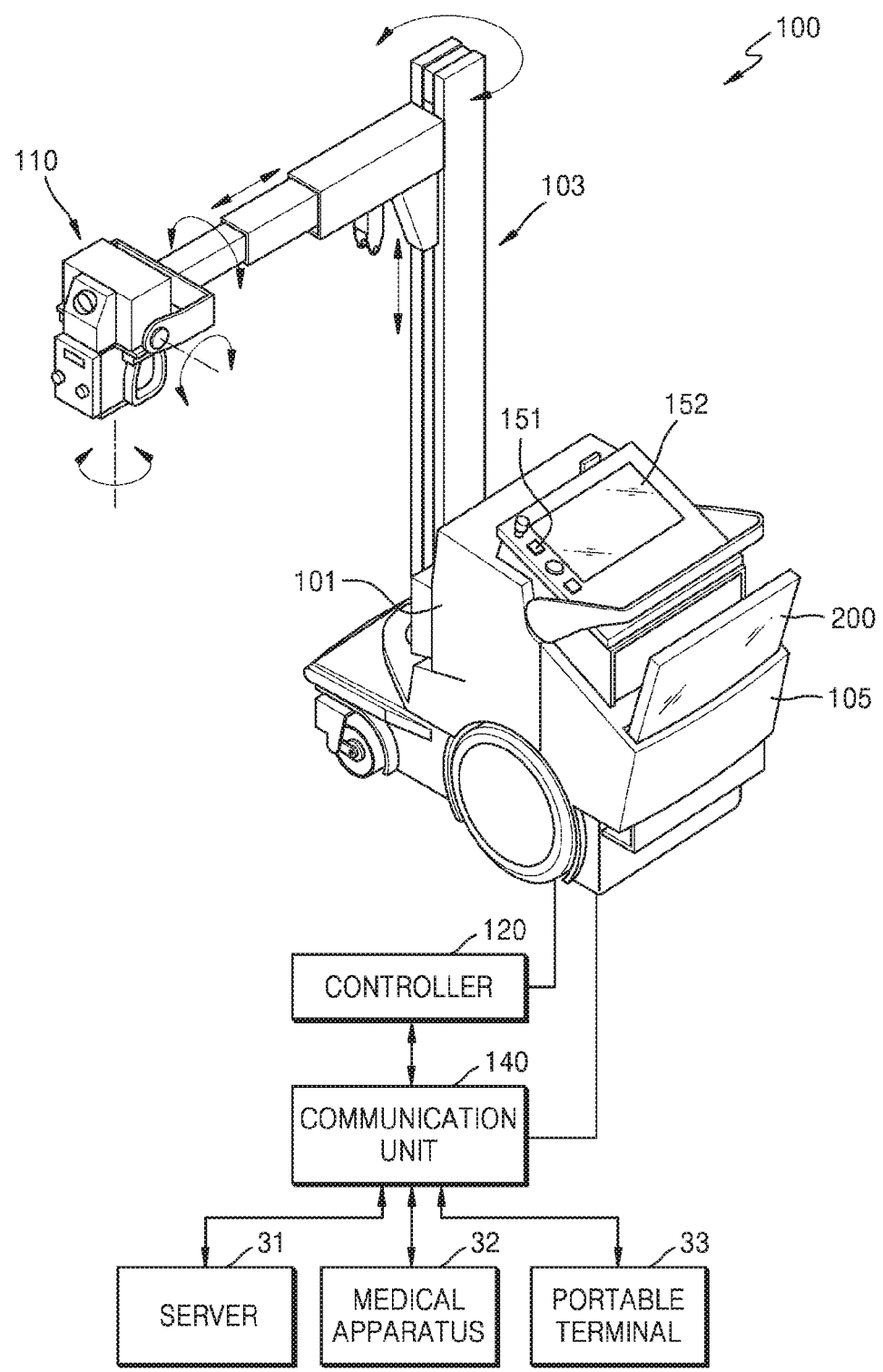
FIG. 1 is an external view and block diagram of an X-ray apparatus, according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

The term "part" or "portion" used herein may be implemented using hardware or software, and according to exemplary embodiments, a plurality of "parts" or "portions" may be formed as a single unit or element, or one "part" or "portion" may include a plurality of units or elements. Expressions such as "at least one of," when preceding a list of elements, modify the entire list of elements and do not modify the individual elements of the list.

In the present specification, an image may include a medical image obtained by a magnetic resonance imaging (MRI) apparatus, a computed tomography (CT) apparatus, an ultrasound imaging apparatus, an X-ray apparatus, or another medical imaging apparatus.

Furthermore, in the present specification, an "object" may be a target to be imaged and may include a human, an animal, or a part of a human or animal. For example, the object may include a body part (an organ, tissue, etc.) or a phantom.

FIG. 1 is an external view and block diagram of an X-ray apparatus 100 implemented as a mobile X-ray apparatus, according to an exemplary embodiment.

Referring to FIG. 1, the X-ray apparatus 100 according to the present exemplary embodiment includes an X-ray radiation device 110 for generating and emitting X-rays, an input device 151 for receiving a command from a user, a display 152 for providing information to the user, a controller 120 for controlling the X-ray apparatus 100 according to the received command, and a communication unit 140, i.e., a communication device or interface, for communicating with an external device.

The X-ray radiation device 110 may include an X-ray source for generating X-rays and a collimator for adjusting a region irradiated with the X-rays generated by the X-ray source.

When the X-ray apparatus 100 is implemented as a mobile X-ray apparatus, a main body 101 connected to the X-ray radiation device 110 is freely movable, and an arm 103 connecting the X-ray radiation device 110 and the main body 101 to each other is rotatable and linearly movable. Thus, the X-ray radiation device 110 may be moved freely in a three-dimensional (3D) space.

The input device 151 may receive commands for controlling imaging protocols, imaging conditions, imaging timing, and locations of the X-ray radiation device 110. The input device 151 may include a keyboard, a mouse, a touch screen, a microphone, a voice recognizer, etc.

The display 152 may display a screen for guiding a user's input, an X-ray image, a screen for displaying a state of the X-ray apparatus 100, and the like.

The controller 120 may control imaging conditions and imaging timing of the X-ray radiation device 110 according to a control command input by the user and generate a medical image based on image data received from an X-ray detector 200. The controller 120 may control a position or orientation of the X-ray radiation device 110 according to imaging protocols and a position of an object.

The controller 120 may include a memory configured to store programs for performing the operations of the X-ray apparatus 100 and a processor or a microprocessor configured to execute the stored programs. The controller 120 may include a single processor or a plurality of processors or microprocessors. When the controller 120 includes the plurality of processors, the plurality of processors may be integrated onto a single chip or be physically separated from one another.

A holder 105 may be formed on the main body 101 to accommodate the X-ray detector 200. A charging terminal may be disposed in the holder 105 to charge the X-ray detector 200. Thus, the holder 105 may be used to accommodate and to charge the X-ray detector 200.

The input device 151, the display 152, the controller 120, and the communication unit 140 may be provided on the main body 101. Image data acquired by the X-ray detector 200 may be transmitted to the main body 101 for image processing, and then the resulting image may be displayed on the display 152 or transmitted to an external device via the communication unit 140.

The controller 120 and the communication unit 140 may be separate from the main body 101, or only some components of the controller 120 and the communication unit 140 may be provided on the main body 101.

The X-ray apparatus 100 may be connected to external devices such as a server 31, a medical apparatus 32, and/or a portable terminal 33 (e.g., a smart phone, a tablet PC, or a wearable device) in order to transmit or receive data via the communication unit 140.

The communication unit 140 may include at least one component that enables communication with an external device. For example, the communication unit 140 may include at least one of a local area communication module, a wired communication module, and a wireless communication module.

The communication unit 140 may receive a control signal from an external device and transmit the received control signal to the controller 120 so that the controller 120 may control the X-ray apparatus 100 according to the received control signal.

Alternatively, by transmitting a control signal to an external device via the communication unit 140, the controller 120 may control the external device according to the transmitted control signal. For example, the external device may process data according to a control signal received from the controller 120 via the communication unit 140.

The communication unit 140 may further include an internal communication module that enables communications between components of the X-ray apparatus 100. A program for controlling the X-ray apparatus 100 may be installed on the external device and may include instructions for performing some or all of the operations of the controller 120.

The program may be preinstalled on the portable terminal 33, or a user of the portable terminal 33 may download the program from a server providing an application for installation. The server for providing an application may include a recording medium having the program recorded thereon.

Figure 2:
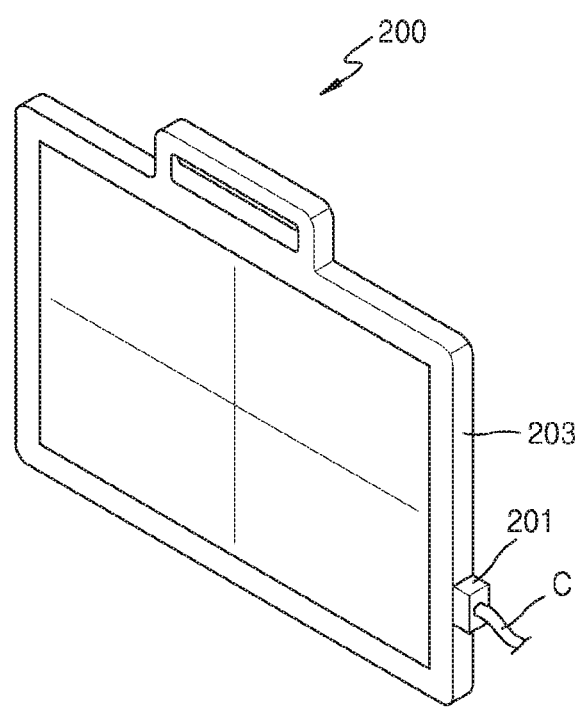
FIG. 2 is an external view of an X-ray detector included in the X-ray apparatus of FIG. 1.

FIG. 2 is an external view of the X-ray detector 200.

As described above, the X-ray detector 200 used in the X-ray apparatus 100 may be implemented as a portable X-ray detector. The X-ray detector 200 may be equipped with a battery for supplying power to operate wirelessly, or as shown in FIG. 2, may operate by connecting a charge port 201 to a separate power supply via a cable C.

A case 203 maintains an external appearance of the X-ray detector 200 and has therein a plurality of detecting elements for detecting X-rays and converting the X-rays into image data, a memory for temporarily or permanently storing the image data, a communication module for receiving a control signal from the X-ray apparatus 100 or transmitting the image data to the X-ray apparatus 100, and a battery. Further, image correction information and intrinsic identification (ID) information of the X-ray detector 200 may be stored in the memory, and the stored ID information may be transmitted together with the image data during communication with the X-ray apparatus 100.

Figure 3:
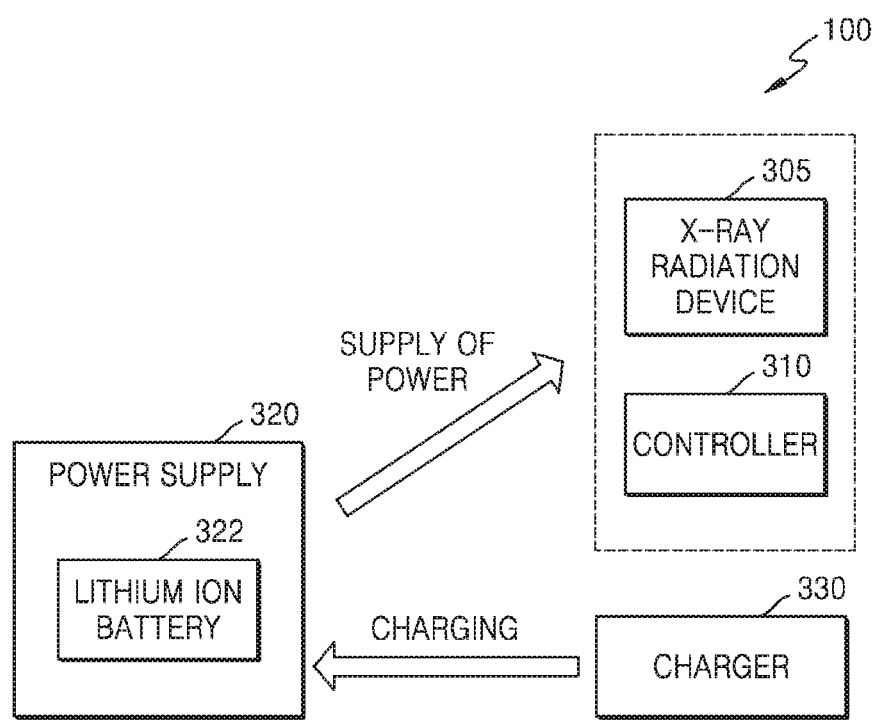
FIG. 3 is a block diagram of an X-ray apparatus according to an exemplary embodiment.

FIG. 3 is a block diagram of an X-ray apparatus 100 according to an exemplary embodiment.

Referring to FIG. 3, the X-ray apparatus 100 according to the present exemplary embodiment may include an X-ray radiation device 305, a controller 310, a power supply 320 including a lithium ion battery 322, and a charger 330. The X-ray apparatus 100 of FIG. 3 may be implemented as a mobile X-ray apparatus as shown in FIG. 1, and FIG. 3 illustrates only components related to the present exemplary embodiment. Thus, as understood by those of ordinary skill in the art, the X-ray apparatus 100 may further include common components in addition to those shown in FIG. 3.

The described-above with respect to the X-ray radiation device 110 and the controller 120 of FIG. 1 may apply to the X-ray radiation device 305 and the controller 310, respectively.

The power supply 320 may supply operating power to the X-ray radiation device 305 and the controller 310 via the lithium ion battery 322. Further, the power supply 320 may supply operating power to the components of the X-ray apparatus 100 that require the operating power. For example, the power supply 320 may supply operating power to the input device 151, the display 152, and the communication unit 140 of the X-ray apparatus 100 via the lithium ion battery 322.

The power supply 320 may control overcurrent that occurs during emission of X-rays by the X-ray radiation device 305. In other words, as the X-ray radiation device 305 emits X-rays, overcurrent that is higher than a normal operating current may flow in the power supply 320, and the power supply 320 may control the overcurrent. According to an exemplary embodiment, in order to control overcurrent, the power supply 320 may include a circuit consisting of a discharge field effect transistor (FET) and a charge FET connected in parallel. According to an exemplary embodiment, in order to control the overcurrent, the power supply 320 may include a circuit including current sensors having different capacities for measuring the amount of discharge current.

The charger 330 may charge the power supply 320. In detail, the charger 330 may supply a charging power to charge the lithium ion battery 322 of the power supply 320. The charging power may be a power generated by the charger 330. According to an exemplary embodiment, the charger 330 may be combined with an external power supply to receive power from the external power supply. The charger 330 may then control the received power according to a user input or arithmetic operations performed within the X-ray apparatus 100, to supply a charging power to the lithium ion battery 322.

The power supply 320, the charger 330, and the controller 310 may each include a communication interface that enables communication therebetween. For example, the power supply 320, the charger 330, and the controller 310 may communicate with one another via their communication interfaces according to a controller area network (CAN) protocol.

The power supply 320, the charger 330, and the controller 310 may each be separately embodied in a different module. Thus, the controller 310 does not need to directly monitor a high voltage, and a high voltage circuit is not needed within the controller 310. This may consequently reduce the risks associated with the high voltage circuit, thereby effectively improving stability. When the power supply 320, the charger 330, and the controller 310 are each composed of a different module, they may be used for different mobile X-ray apparatuses and thus share a common platform. Further, by applying a shielded case to each separate module of the power supply 320, the charger 330, and the controller 310, it is possible to suppress Electro Magnetic Interference (EMI)/Electro Magnetic Compatibility (EMC) noise that may occur therebetween.

Figure 4:
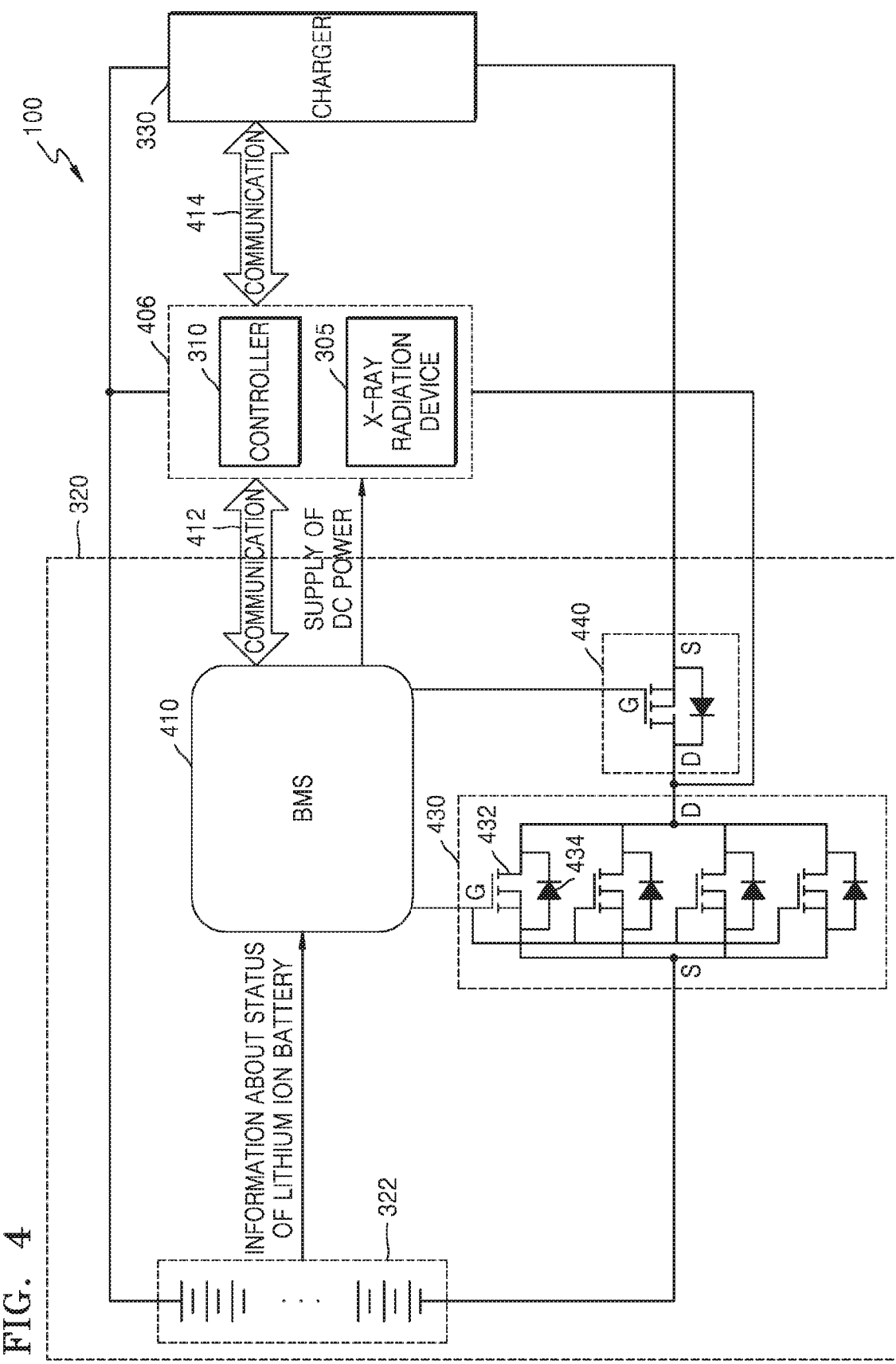
FIG. 4 is a schematic diagram of an X-ray apparatus according to an exemplary embodiment.

FIG. 4 illustrates an X-ray apparatus 100 according to an exemplary embodiment.

Referring to FIG. 4, a power supply 320 may include a lithium ion battery 322, a battery management system (BMS) 410, a discharge FET 430, and a charge FET 440. FIG. 4 illustrates only components related to the present exemplary embodiment. Thus, one of ordinary skill in the art will understand that the X-ray apparatus 100 may further include common components other than those shown in FIG. 4.

The lithium ion battery 322 is a type of secondary battery that includes a combination of a plurality of battery cells connected to each other. For example, the lithium ion battery 322 may include a total of 352 cells, e.g., a serial connection of 88 cells which are connected in parallel as 4 strings, e.g., 4 parallel cell groups each including 88 serially connected cells.

The BMS 410 may detect a state of the lithium ion battery 322, such as a voltage and a temperature thereof. According to an exemplary embodiment, the BMS 410 may include a battery stack monitor circuit designed to monitor a voltage of the lithium ion battery 322 and a temperature of a battery cell. The BMS 410 may control and manage the power supply 320 based on the state of the lithium ion battery 322. The BMS 410 may control on/off states of the charge FET 440 and the discharge FET 430 to manage a charge path and a discharge path, respectively.

The BMS 410 may operate a protection circuit based on the state of the lithium ion battery 322. In other words, the BMS 410 may operate the protection circuit to protect the lithium ion battery 322. In detail, based on the state of the lithium ion battery 322, the BMS 410 may operate the protection circuit to protect the lithium ion battery 322 against at least one of over-discharge, overcurrent, overheating, and unbalancing between battery cells.

The BMS 410 may operate the protection circuit when the lithium ion battery 322 is in an over-discharged state where a voltage of the lithium ion battery 322 is lower than a reference voltage. For example, if a voltage of the lithium ion battery 322 drops to less than or equal to 275V, the BMS 410 may operate a shutdown circuit to turn itself off. The BMS 410 may operate the protection circuit when the lithium ion battery 322 is in an overcurrent state where a current of the lithium ion battery 322 is higher than a reference value. For example, if the current of the lithium ion battery 322 is greater than or equal to 40 A, the BMS 410 may operate a shutdown circuit to reset itself. The BMS 410 may operate the protection circuit when the lithium ion battery 322 is in an overheated state where a temperature of the lithium ion battery 322 is higher than a reference value. For example, if the temperature of the lithium ion battery 322 is greater than or equal to 70° C., the BMS 410 may operate the protection circuit to shut off a charge path and a discharge path. Further, when the lithium ion battery 322 is unbalanced between cells, the BMS 410 may operate the protection circuit. For example, if a voltage difference between cells in the lithium ion battery 322 remains greater than or equal to 1.5 V for 10 seconds or more, the BMS 410 may operate a shutdown circuit to turn itself off.

The BMS 410 may communicate with a controller 310 via a communication interface 412, e.g., according to a CAN protocol. Further, the charger 330 may communicate with the controller 310 via a communication interface 414, e.g., according to the CAN protocol. The BMS 410 may supply a DC power to each component of the X-ray apparatus 100 including the controller 310.

The discharge FET 430 may include a plurality of FETs 432 connected in parallel. Since overcurrent may flow in the power supply 320 during X-ray emission by the X-ray radiation device 305, the FETs having a specific capacity in the discharge FET 430 may be connected in parallel. In other words, by connecting the FETs having the specific capacity in parallel, a maximum allowable current capacity of the discharge FET 430 may be increased. For example, if overcurrent greater than or equal to 300 A flows within the power supply 320 during X-ray emission by the X-ray radiation device 305, the discharge FET 430 may include 4 FETs which are connected in parallel and have a capacity of 100 A each for the protection against the overcurrent.

According to an exemplary embodiment, the discharge FET 430 and the charge FET 440 may each include N-channel FETs.

The discharge FET 430 and the charge FET 440 may control a path of discharge or charge current when the lithium ion battery 322 is discharged or charged. According to an exemplary embodiment, when the lithium ion battery 322 is discharged, the charge FET 440 is turned off, and a discharge current loop may be formed by the discharge FET 430. According to an exemplary embodiment, when the lithium ion battery 322 is charged, the discharge FET 430 is turned off, and a charge current loop may be formed by a diode or diodes 434 included in the discharge FET 430 and the charge FET 440. Further, the lithium ion battery 322 may be discharged and charged at the same time via the discharge FET 430 and the charge FET 440.

While FIG. 4 shows that a load 406 for receiving a power from the lithium ion battery 322 includes the controller 310 and the X-ray radiation device 305, the load 406 may further include other components of the X-ray apparatus 100 that require power.

Figure 5:
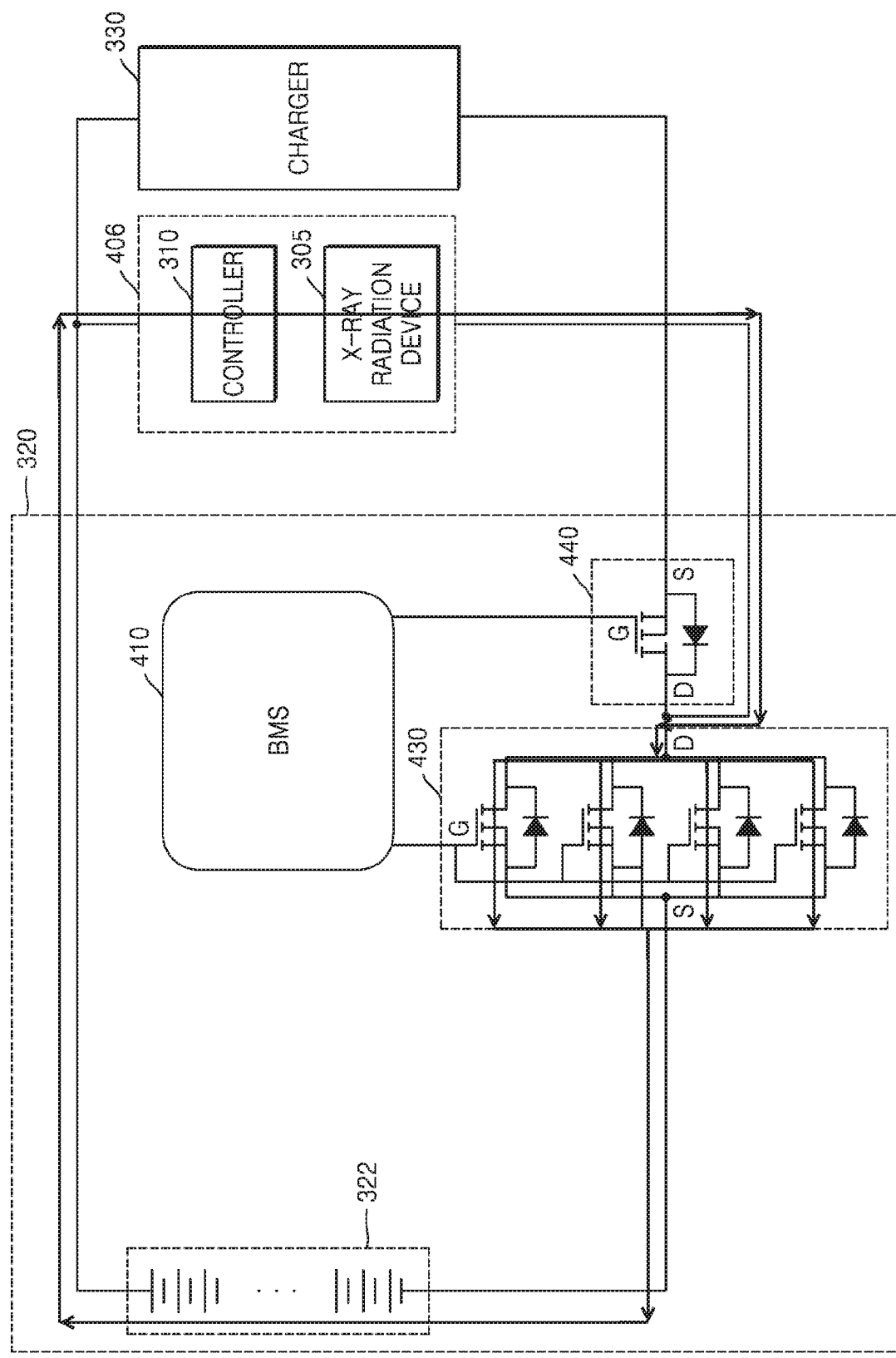
FIG. 5 is a schematic diagram illustrating discharging of a lithium ion battery according to an exemplary embodiment.

FIG. 5 is a schematic diagram illustrating discharging of a lithium ion battery 322 according to an exemplary embodiment When the lithium ion battery 322 is discharged, a charge FET 440 is turned off since a source (S) voltage of the charge FET 440 is higher than a drain (D) voltage. Further, a discharge FET 430 is turned on since a drain (D) voltage of the discharge FET 430 is higher than a source (S) voltage.

Thus, as shown in FIG. 5, a discharge current loop may be formed in a clockwise direction in which a discharge current flows through a load 406, the discharge FET 430, and the lithium ion battery 322. Further, even when the charge FET 440 is turned off, discharging of the lithium ion battery 322 may be performed normally.

Figure 6:
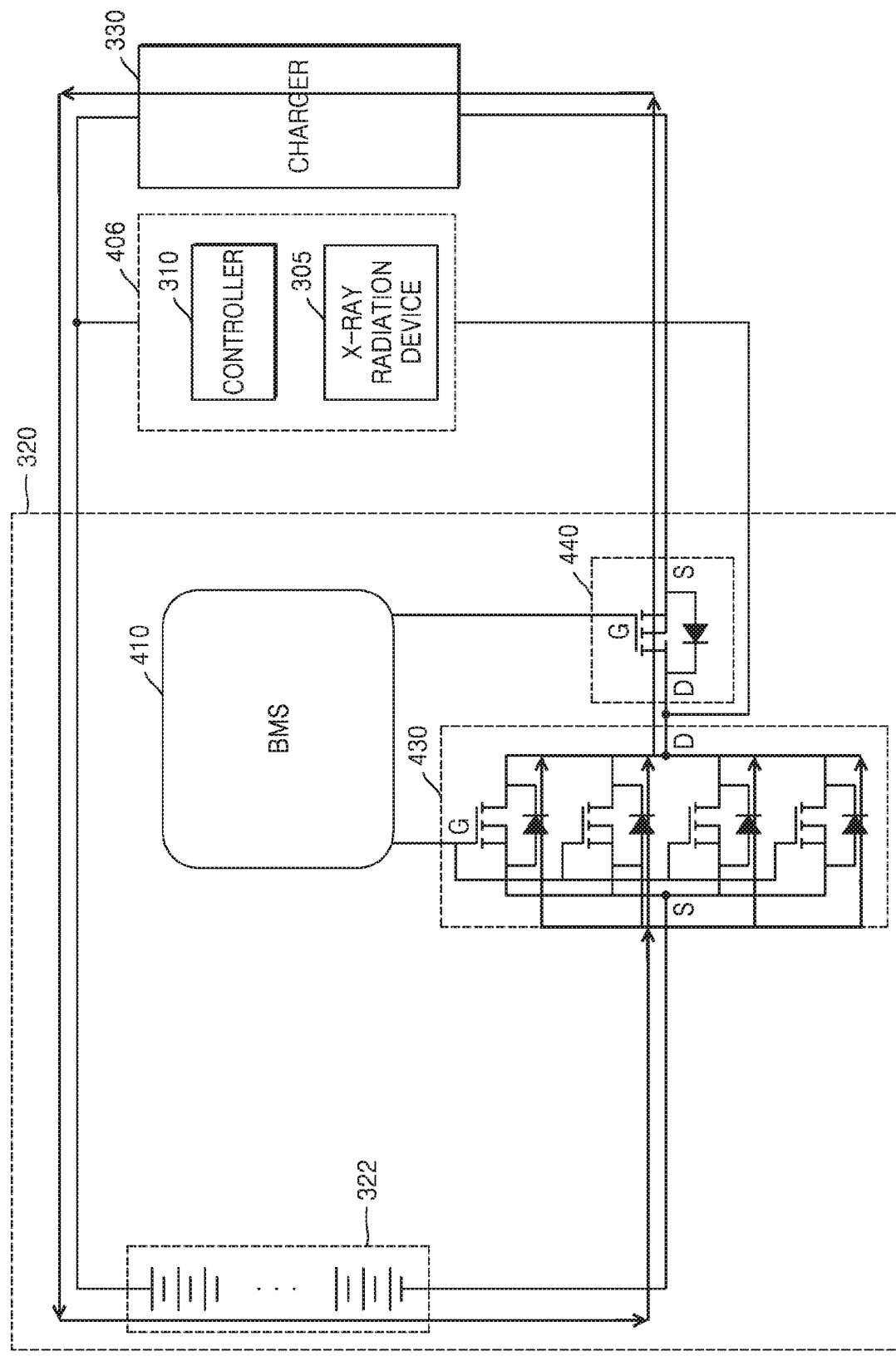
FIG. 6 is a schematic diagram illustrating charging of a lithium ion battery according to an exemplary embodiment.

FIG. 6 is a schematic diagram illustrating charging of a lithium ion battery 322 according to an exemplary embodiment.

When the lithium ion battery 322 is charged, a discharge FET 430 is turned off since a source (S) voltage of the discharge FET 430 is higher than a drain (D) voltage thereof. When the discharge FET 430 is turned off, a charge current may flow through a diode 434 of the discharge FET 430. Further, when the lithium ion battery 322 is charged, a charge FET 440 is turned on since a drain (D) voltage of the charge FET 440 is higher than a source (S) voltage thereof.

Thus, as shown in FIG. 6, a charge current loop may be formed in a counter-clockwise direction in which a charge current flows through a charger 330, the lithium ion battery 322, a diode 434 of the discharge FET 430, and the charge FET 440. Further, even when the discharge FET 430 is turned off, charging of the lithium ion battery 322 may be performed normally.

Figure 7:
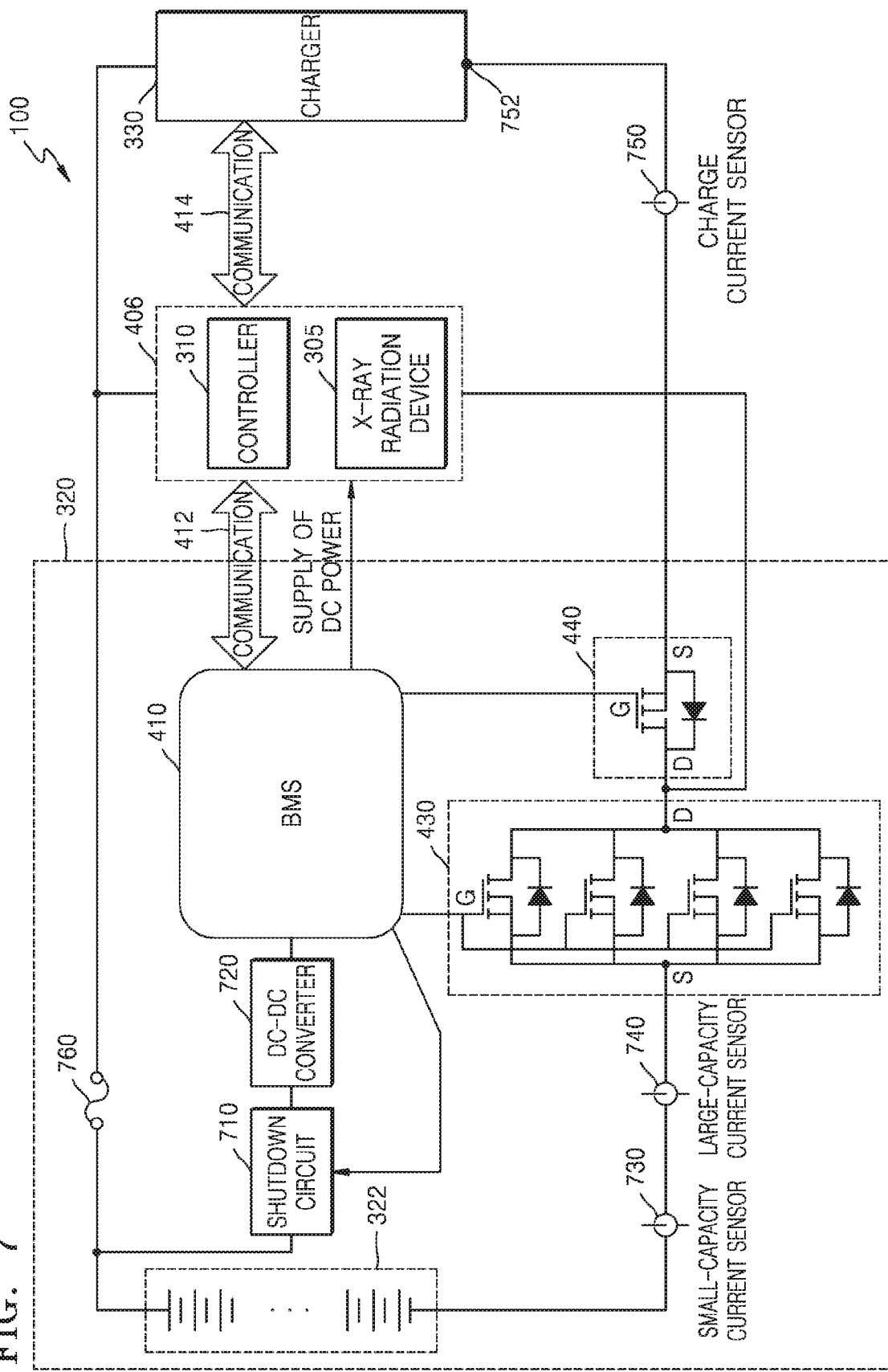
FIG. 7 is a schematic diagram of an X-ray apparatus according to an exemplary embodiment.

FIG. 7 is a schematic diagram of an X-ray apparatus 100 according to an exemplary embodiment.

Referring to FIG. 7, a power supply 320 may include a lithium ion battery 322, a BMS 410, a discharge FET 430, a charge FET 440, a shutdown circuit 710, a small-capacity current sensor 730, e.g., a first current sensor, a large-capacity current sensor 740, e.g., a second current sensor, a DC-to-DC (DC-DC) converter 720, and a fuse 760. The X-ray apparatus 100 may include a charge current sensor 750, e.g., a third current sensor. Since the lithium ion battery 322, the BMS 410, the discharge FET 430, and the charge FET 440 respectively correspond to the lithium ion battery 322, the BMS 410, the discharge FET 430, and the charge FET 440 described with reference to FIG. 4, detailed descriptions thereof will be omitted below.

The BMS 410 may detect current of the lithium ion battery 322 by using the current sensors having different capacities, i.e., the small-current sensor and large-capacity current sensor 730 and 740. In detail, the BMS 410 may detect current flowing in the lithium ion battery 322 by using the small-capacity current sensor 730. When overcurrent flows in the lithium ion battery 322, the BMS 410 may detect overcurrent flowing in the lithium ion battery 322 by using the large-capacity current sensor 740.

The BMS 410 may detect, via the small-capacity current sensor 730, current flowing in the lithium ion battery 322 by activating the small-capacity current sensor 730 while deactivating the large-capacity current sensor 740. Then, when an X-ray radiation device 305 emits X-rays, the BMS 410 may detect overcurrent that occurs during the X-ray emission via the large-capacity current sensor 740 by activating the large-capacity current sensor 740 while deactivating the small-capacity current sensor 730. Subsequently, when the X-ray emission is completed, the BMS 410 may detect, via the small-capacity current sensor 730, current flowing in the lithium ion battery 322 by activating the small-capacity current sensor 730 while deactivating the large-capacity current sensor 740. According to an exemplary embodiment, the BMS 410 may receive an X-ray emission preparation signal from a controller 310 and activate the large-capacity current sensor 740 to detect overcurrent occurring during X-ray emission via the large-capacity current sensor 740.

The BMS 410 may check the residual amount of the lithium ion battery 322 based on the amount of current detected using the small-current sensor and large-capacity current sensor 730 and 740. In detail, the BMS 410 may use Coulomb counting based gauging to check the residual amount of the lithium ion battery 322 based on the detected amount of current.

The X-ray apparatus 100 may further include the charge current sensor 750 for measuring a charge current at an output terminal 752 of the charger 330. When the lithium ion battery 322 is charged and discharged at the same time, current measured by the small-current sensor and large-capacity current sensor 730 or 740 may be a sum of a discharge current and a charge current. Thus, in order to accurately measure a discharge current and a charge current, the X-ray apparatus 100 may measure the charge current by using the charge current sensor 750.

The BMS 410 may receive signals indicating that the X-ray radiation device 305 starts emission of X-rays and that the X-ray radiation device 305 completes the emission of X-rays from the controller 310 via a communication interface 412.

The BMS 410 may turn itself off by using the shutdown circuit 710, e.g., by using a switch included therein. When the BMS 410 may check a state of the lithium ion battery 322 to detect hazardous conditions such as over-discharge and overcharge, the BMS 410 may turn itself off by using the shutdown circuit 710 that serves as a protection circuit. When the BMS 410 turns itself off, the power being supplied to the controller 310 is also cut off, so that the controller 310 may turn off.

The fuse 760 is designed to stop continuous flowing of excessive current that is greater than a nominal value in the power supply 320 and may protect a battery cell when the lithium ion battery 322 is subjected to an external short circuit.

The DC-DC converter 720 may convert a voltage of the lithium ion battery 322 into an operating voltage of the BMS 410 or a DC power of the components of the X-ray apparatus 100.

Figure 8:
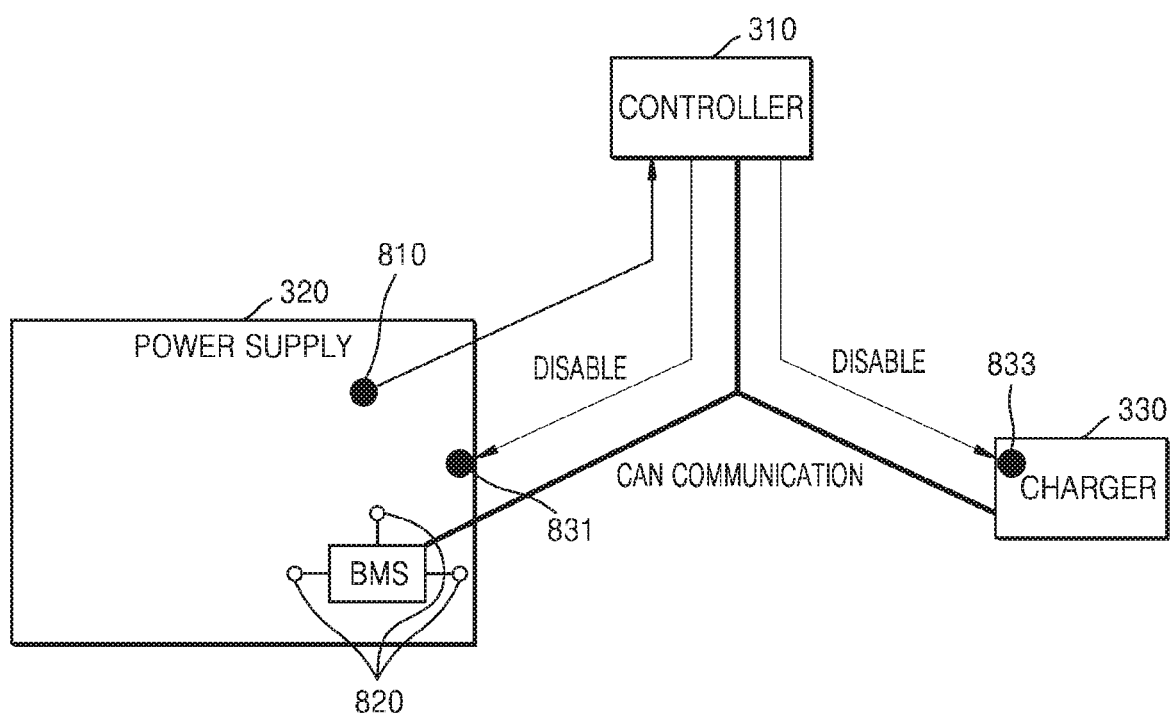
FIG. 8 is a schematic diagram of an X-ray apparatus according to an exemplary embodiment.

FIG. 8 is a schematic diagram of an X-ray apparatus according to an exemplary embodiment.

Referring to FIG. 8, a power supply 320, a controller 310, and a charger 330 may each include a communication interface and communicate with one another via their communication interfaces. For example, the power supply 320, the controller 310, and the charger 330 may communicate with one another according to a CAN protocol.

The power supply 320 may include a BMS-only temperature sensor 820, e.g., a first temperature sensor. The BMS 410 may use the BMS-only temperature sensor 820 to monitor a temperature of the power supply 320 and determine whether the power supply 320 is overheated. For example, if the power supply 320 is overheated to a temperature higher than a specific threshold value, the BMS 410 may operate a protection circuit that cuts off a charge path and a discharge path. As illustrated, the BMS-only temperature sensor 820 may include three sensors or three sensing points, but this is not limiting.

The power supply 320 may further include a controller-only temperature sensor 810, e.g., a second temperature sensor, that may be directly monitored by the controller 310. If a communication error occurs between the controller 310 and the BMS 410, the controller 310 might not be able to receive temperature information of the power supply 320 from the BMS 410. The controller 310 may monitor the temperature of the power supply 320 independently via the controller-only temperature sensor 810. Thus, when a communication error occurs, the controller 310 may determine whether to turn off the BMS 410 by using the controller-only temperature sensor 810 without a need to forcibly turn off the BMS 410.

The power supply 320 and the charger 330 may respectively include first and second interrupt pins 831 and 833 that can be directly controlled by the controller 310. The controller 310 may respectively transmit disable signals to the power supply 320 and the charger 330 via the first and second interrupt pins 831 and 833, and accordingly turn off the power supply 320 and the charger 330. Thus, when it is determined that a temperature of the power supply 320 is equal to or higher than a specific threshold value via the controller-only temperature sensor 810, the controller 310 may forcibly turn off the power supply 320 and the charger 330 via the first and second interrupt pins 831 and 833, respectively.

When the BMS 410 operates a shutdown circuit to turn itself off, a shutdown signal from the BMS 410 may be transmitted to the controller 310. After receiving the shutdown signal, the controller 310 may monitor whether the BMS 410 is shut down for a specific amount of time. If the BMS 410 is not shut down for the specific amount of time as a result of monitoring, the controller 310 may forcibly turn off the BMS 410 via the first interrupt pin 831. For example, after the BMS 410 activates a shutdown bit, the controller 310 may monitor whether the BMS 410 is shut down for 10 seconds. If the BMS 410 is not shut down for 10 seconds, the controller 310 may forcibly turn off the BMS 410 via the first interrupt pin 831.

Figure 9:
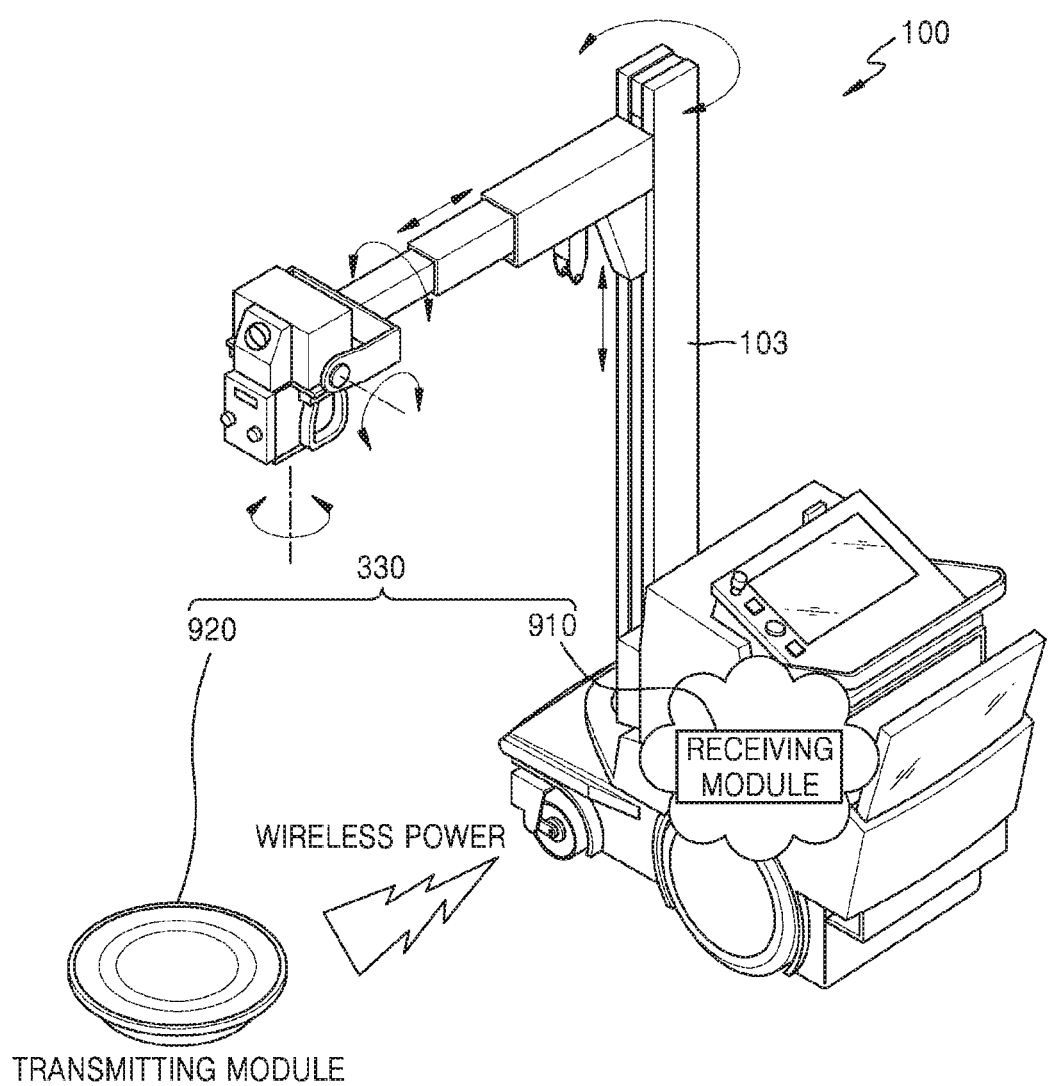
FIG. 9 illustrates a charger according to an exemplary embodiment.

FIG. 9 illustrates an X-ray apparatus according to an exemplary embodiment.

According to an exemplary embodiment, the charger 330 may include a wireless charging system including a transmitting module 920, e.g., a transmitter, and a receiving module 910, e.g., a receiver. For example, the charger 330 may be a self-inductive wireless charging system. In the charger 330, the transmitting module 920 may convert an AC power from an external power supply into a DC power, amplify the DC power, and transmit the amplified DC power wirelessly to the receiving module 910 via a transmitting coil. The receiving module 910 may rectify the received power to charge the lithium ion battery 322.

As another example, the receiving module 910 of the charger 330 may receive a power transmitted wirelessly by the transmitting module 920 installed externally to the receiving module 910 and may rectify the received power to charge the lithium ion battery 322. Thus, an X-ray apparatus 100 including the charger 330 may be located near the transmitting module 920 and may charge the lithium ion battery 322 by using the power transmitted wirelessly by the transmitting module 920.

Figure 10:
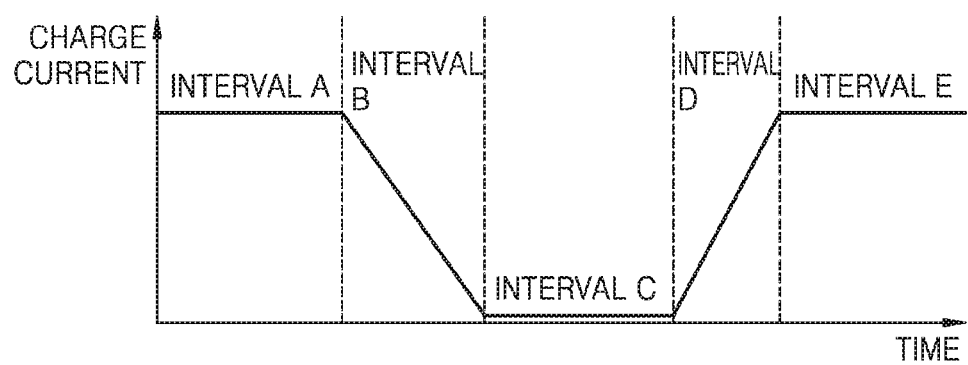
FIG. 10 is a timing diagram of an operation of charging a lithium ion battery according to an exemplary embodiment.

FIG. 10 is a timing diagram of an operation of charging a lithium ion battery 322 according to an exemplary embodiment.

First, during interval A, as the charger 330 performs a charging operation, a charge voltage may increase while a charge current remains constant.

Thereafter, during interval B, as the lithium ion battery 322 relaxes, the charge current may decrease.

An interval C indicates a low current state in which a charge current less than a specific threshold value remains for a specific amount of time. The charger 330 may detect the low current state, as will be described in detail below with reference to FIG. 11. If the low current state is detected for a specific amount of time or a specific number of times, the charger 330 may stop a charging operation. For example, if the charger 330 detects a low current state, in which the charge current is less than or equal to 0.5 A, 10 times, the charger 330 may stop a charging operation. Thus, if the lithium ion battery 322 relaxes, the charger 330 may stop the charging operation, thereby preventing unnecessary power consumption.

Subsequently, during interval D, when a voltage of the lithium ion battery 322 drops to a preset value, the charger 330 may restart the charging operation, and the charge current may also increase.

Thereafter, during interval E, which corresponds to the interval A, as the charger 330 performs the charging operation, the charge voltage may increase while the charge current remains constant.

Figure 11:
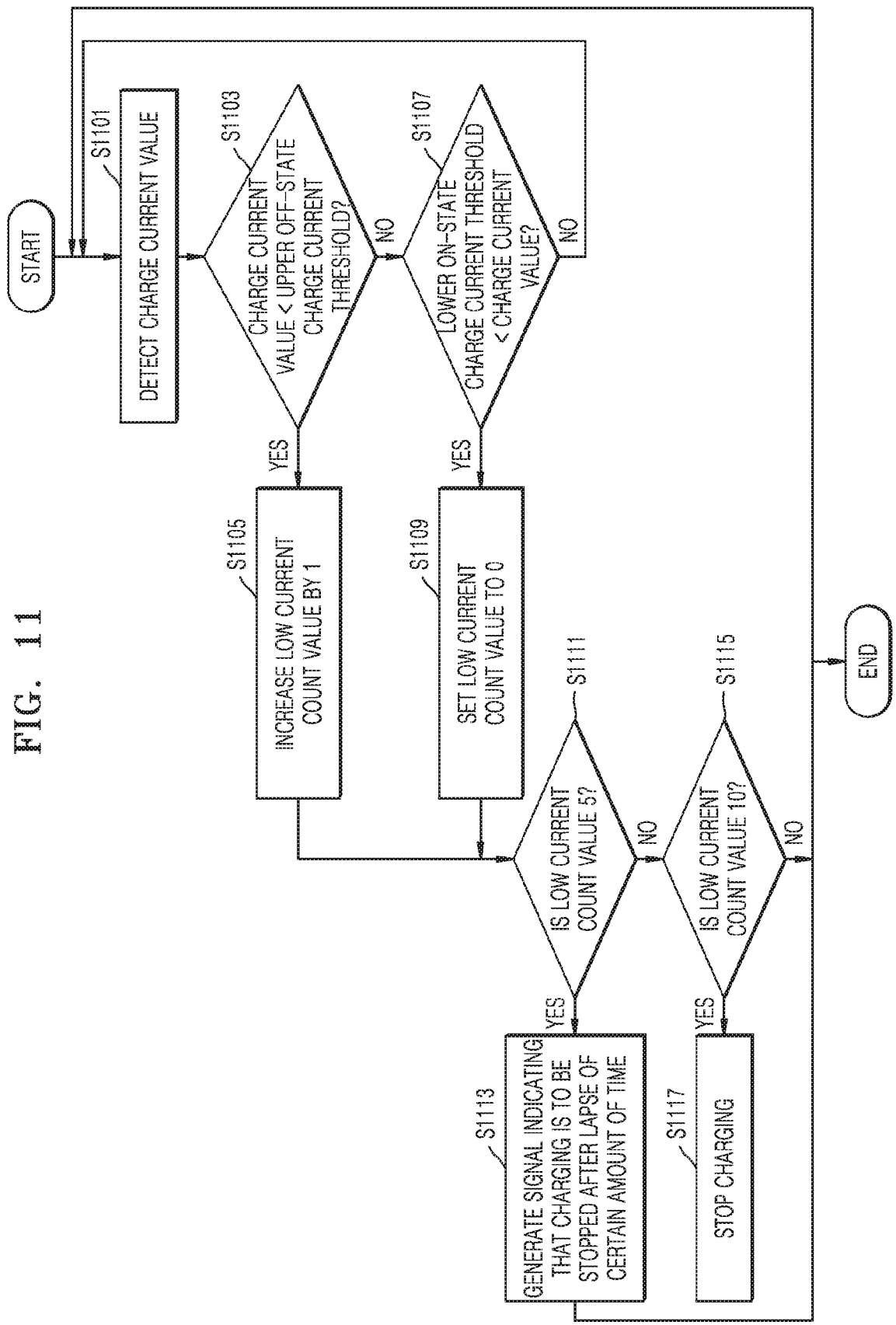
FIG. 11 is a flowchart of a method of sensing of a low current state by a charger, according to an exemplary embodiment.

FIG. 11 is a flowchart of a method of sensing of a low current state by the charger 330, according to an exemplary embodiment.

The charger 330 may detect a charge current value (operation S1101).

The charger 330 may determine whether the detected charge current value is less than an upper off-state charge current threshold (operation S1103). For example, the upper off-state charge current may be 0.5 A.

If the detected charge current value is less than the upper off-state charge current threshold in operation S1103, the charger 330 may increase a low current count value by 1 (operation S1105). In other words, if the low current count value is increased by 1 each cycle to reach a certain count value, e.g., 10, the charger 330 may determine that the current has remained low for a certain amount of time.

Otherwise, if the detected charge current value is not less than the upper off-state charge current threshold in operation S1103, the charger 330 may determine whether the detected charge current value is greater than a lower on-state charge current threshold (operation S1107). For example, the lower on-state charge current threshold may be 0.8 A.

If the detected charge current value is greater than the lower on-state charge current threshold in operation S1107, the charger 330 may set the low current count value to 0 (operation S1109).

Otherwise, if the detected charge current value is not greater than the lower on-state charge current threshold in operation S1107, the charger 330 may detect a charge current value (operation S1101).

The charger 330 may determine whether the low current count value is five 5 (operation S1111).

If the low current count value is 5 in operation S1111, the charger 330 may generate a signal indicating that a charging operation is to be stopped after a lapse of a certain amount of time (operation S1113).

Otherwise, if the low current count value is not 5 in operation S1111, the charger 330 may determine whether the low current count value is 10 (operation S1115).

If the low current count value is 10 in operation S1115, the charger 330 may stop the charging operation (operation S1117). In other words, if the low current count value is 10, the charger 330 may determine that the low current state has remained for the certain amount of time and then stop the charging operation.

Otherwise, if the low current count value is not 10 in operation S1115, the charger 330 may detect a charge current value (operation S1101).

Exemplary embodiments may be implemented through non-transitory computer-readable recording media having recorded thereon computer-executable instructions and data. The non-transitory computer-readable medium may include a compact disc (CD), a digital versatile disc (DVD), a hard disc, a Blu-ray disc, a universal serial bus (USB), a memory card, a read only memory (ROM), and the like. The instructions may be stored as program codes, and when executed by a processor, may generate a predetermined program module to perform a specific operation. When being executed by the processor, the instructions may perform specific operations according to the exemplary embodiments.

The foregoing exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. A mobile X-ray apparatus comprising:
an X-ray radiation device configured to emit X-rays;
a controller configured to control the X-ray radiation device;
a power supply configured to supply operating power to the X-ray radiation device and the controller; and
a charger configured to charge the power supply, and
wherein the power supply comprises:
a lithium ion battery including a plurality of battery cells,
a current sensor configured to detect current of the lithium ion battery, and
a battery management system (BMS) configured to detect an occurrence of an overcurrent in the lithium ion battery via the current sensor in response to receiving an X-ray emission preparation signal, and to control the overcurrent that occurs during emission of X-rays.

2. The mobile X-ray apparatus of claim 1, wherein the power supply further comprises a temperature sensor configured to detect a temperature of the power supply, and
wherein the BMS is further configured to control a charge current path to be an off-state based on the temperature detected by the temperature sensor being higher than a threshold value.

3. The mobile X-ray apparatus of claim 2, wherein the BMS is further configured to control an on-state or an off-state of a discharge current path in which a discharge current flows from the lithium ion battery to the controller and the X-ray radiation device, and
wherein the power supply is further configured to supply the operating power to the X-ray radiation device and the controller via the discharge current path being in the on-state.

4. The mobile X-ray apparatus of claim 2, wherein the power supply further comprises a charge switch connected to the charger and configured to be turned on and off, and
based on the charge switch turned on, the charge current path in which a charge current flows from the charger to the lithium ion battery is in an on-state.

5. The mobile X-ray apparatus of claim 4, wherein the power supply further comprises a discharge switch connected to the lithium ion battery and used to form a discharge current path, and
wherein the discharge current path is a current path in which a discharge current flows from the lithium ion battery to the controller and the X-ray radiation device.

6. The mobile X-ray apparatus of claim 5, wherein the discharge switch includes a plurality of FETs connected in parallel to one another.

7. The mobile X-ray apparatus of claim 5, wherein the BMS is further configured to detect a state of the power supply, to control the charge current path by turning off the discharge switch and turning on the charge switch, and control the discharge current path by turning on the discharge switch and turning off the charge switch.

8. The mobile X-ray apparatus of claim 1, wherein the power supply further comprises:
a temperature sensor configured to detect a temperature of the power supply,
wherein the temperature sensor is directly monitored by the controller.

9. The mobile X-ray apparatus of claim 1, wherein the BMS is further configured to control an operation of a protection circuit for protection against at least one from among an over-discharge, the overcurrent, an overheating, and an unbalance between at least two cells among the plurality of battery cells included in the lithium ion battery.

10. The mobile X-ray apparatus of claim 1, wherein the current sensor includes a first current sensor configured to detect a first current, and
wherein the BMS is further configured to detect a value of the overcurrent in the lithium ion battery via the first current sensor in response to receiving the X-ray emission preparation signal.

11. The mobile X-ray apparatus of claim 10, wherein the power supply further includes a second current sensor configured to detect a second current smaller than the first current.

12. The mobile X-ray apparatus of claim 1, wherein each of the controller, the power supply, and the charger includes a respective communication interface, and
the controller, the power supply, and the charger are configured to communicate with one another via the respective communication interface.

13. The mobile X-ray apparatus of claim 12, wherein the respective communication interface performs communication according to a controller area network (CAN) protocol.

14. The mobile X-ray apparatus of claim 1, wherein the charger includes a wireless charging system including, a transmitter and a receiver.

15. The mobile X-ray apparatus of claim 1, wherein the charger is further configured to receive power wirelessly from an external device and charge the lithium ion battery based on the received power.

16. The mobile X-ray apparatus of claim 1, wherein the power supply further comprises:
a shutdown circuit configured to turn off the BMS;
a discharge switch connected to the lithium ion battery and used to form a discharge current path; and
a charge switch connected to the charger and configured to turn on and off to charge the lithium ion battery.

17. A mobile X-ray apparatus comprising:
an X-ray radiation device configured to emit X-rays;
a controller configured to control the X-ray radiation device;
a power supply configured to supply operating power to the X-ray radiation device and the controller; and
a charger configured to charge the power supply, and
wherein the power supply comprises:
a lithium ion battery including a plurality of battery cells,
a current sensor configured to detect current of the lithium ion battery,
a temperature sensor configured to detect a temperature of the power supply, and
a battery management system (BMS) configured to detect an occurrence of an overcurrent in the lithium ion battery via the current sensor in response to receiving an X-ray emission preparation signal, and
wherein, the controller is further configured to directly monitor information about the temperature of the power supply detected by the temperature sensor.

* * * * *